(12) United States Patent
Nishikaze et al.

(10) Patent No.: US 11,971,336 B2
(45) Date of Patent: Apr. 30, 2024

(54) METHOD FOR PREPARING SAMPLE AND ANALYSIS METHOD

(71) Applicant: SHIMADZU CORPORATION, Kyoto (JP)

(72) Inventors: Takashi Nishikaze, Kyoto (JP); Hisatoshi Hanamatsu, Sapporo (JP); Jun-ichi Furukawa, Sapporo (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 16/289,643

(22) Filed: Feb. 28, 2019

(65) Prior Publication Data

US 2019/0271617 A1 Sep. 5, 2019

(30) Foreign Application Priority Data

Mar. 1, 2018 (JP) .................. 2018-036367

(51) Int. Cl.
| | |
|---|---|
| G01N 1/30 | (2006.01) |
| C08B 37/00 | (2006.01) |
| G01N 30/06 | (2006.01) |
| G01N 33/50 | (2006.01) |
| G01N 33/68 | (2006.01) |
| H01J 49/00 | (2006.01) |

(52) U.S. Cl.
CPC .......... *G01N 1/30* (2013.01); *C08B 37/0006* (2013.01); *G01N 30/06* (2013.01); *G01N 33/50* (2013.01); *G01N 33/6848* (2013.01); *H01J 49/0027* (2013.01); *G01N 2400/00* (2013.01)

(58) Field of Classification Search
None
See application file for complete search history.

(56) References Cited

U.S. PATENT DOCUMENTS

2018/0059094 A1   3/2018   Nishikaze

FOREIGN PATENT DOCUMENTS

| CN | 107430113 A | 12/2017 |
|---|---|---|
| EP | 3 279 655 A1 | 2/2018 |
| JP | 6135710 B2 | 5/2017 |

OTHER PUBLICATIONS

Cho, C-C. et al. Direct Amidation of Aldoses and Decarboxylative Amidation of r-Keto Acids: An Efficient Conjugation Method for Unprotected Carbohydrate Molecules, Journal of Organic Chemistry, 74, 1549-1556 (Year: 2009).*

(Continued)

*Primary Examiner* — Xiaoyun R Xu
(74) *Attorney, Agent, or Firm* — FOLEY & LARDNER LLP

(57) ABSTRACT

A method for preparing a sample comprising a glycan includes: performing a lactonization reaction in which at least a part of sialic acids included in the glycan is lactonized; and performing an amidation reaction in which lactones of lactonized sialic acids are amidated through addition of an amidation reaction solution to the sample, the amidation reaction solution comprising at least one selected from the group consisting of ammonia, an amine, and a salt thereof that is reacted with the lactonized sialic acids.

16 Claims, 9 Drawing Sheets

(56) References Cited

OTHER PUBLICATIONS

Holst et al., "Linkage-Specific in Situ Sialic Acid Derivatization for N-Glycan Mass Spectrometry Imaging of Formalin-Fixed Paraffin-Embedded Tissues," Analytical Chemistry 2016, 86, pp. 5904-5913.
Ishibashi et al., "A Novel Endoglycoceramidase Hydrolyzes Oligogalactosylceramides to Produce Galactooligosaccharides and Ceramides," Journal of Biological Chemistry, vol. 282, No. 15, pp. 11386-11396 (2007).
Li et al., "MALDI-MS analysis of sialylated N-glycan linkage isomers using solidphase two step derivatization method," Analytica Chimica Acta 924, pp. 77-85 (2016).
Nishikaze et al., "Differentiation of Sialyl Linkage Isomers by One-Pot Sialic Acid Derivatization for Mass Spectrometry-Based Glycan Profiling," Analytical Chemistry 2017, 89, pp. 2353-2360.
Nishikaze et al.,"A universal approach to linkage-specific derivatization for sialic acids on glycopeptides," ASMS 2017.
Extended European Search Report issued in European Patent Application No. 19159291, dated May 28, 2019.
Noortje De Haan et al: "Linkage-Specific Sialic Acid Derivatization for MALDI-TOF-MS Profiling of IgG Glycopeptides", Analytical Chemistry, vol. 87, No. 16, Jul. 31, 2015, pp. 8284-8291.
Takashi Nishikaze: "Sensitive and Structure-Informative N-Glycosylation Analysis by MALDI-MS; Ionization, Fragmentation, and Derivatization", Mass Spectrometry, vol. 6, No. A0060, Aug. 7, 2017,pp. 1-12.
First Office Action dated Aug. 25, 2021 issued in CN Application No. 201910123558.1, with English translation, 18 pages.
Second Office Action dated Feb. 28, 2022 issued in CN Application No. 2019 1012 3558.1, with English translation, 16 pages.
Notice of Allowance dated Oct. 19, 2022 issued in Chinese Application No. 201910123558.1, with English translation, 4 pages.
Notice of Allowance dated May 9, 2023 issued in corresponding European Application No. 19159291.4, 44 pages.

\* cited by examiner

METHOD FOR PREPARING SAMPLE AND ANALYSIS METHOD

INCORPORATION BY REFERENCE

The disclosure of the following priority application is herein incorporated by reference: Japanese Patent Application No. 2018-036367 filed Mar. 1, 2018

TECHNICAL FIELD

The present invention relates to a method for preparing a sample, and an analysis method.

BACKGROUND ART

Sialic acid is a saccharide abundant in the biological body. Sialic acid is included in glycans linked to protein in the biological body, and is often present at an end (non-reducing end) of a glycan. Thus, sialic acid is positioned in the outermost side of such a glycoprotein molecule, and plays an important role because it is directly recognized by other molecules.

Sialic acid may have different linkage types to the adjacent saccharide. For example, α2,3- and α2,6-linkage types are primarily known for human N-linked glycans, and in addition to these linkage types, α2,8- and α2,9-linkage types are known for O-linked glycans and glycosphingolipids. Sialic acids with such different linkage types are recognized by different molecules, and thus can play different roles. In addition, sialic acid in expressed glycoprotein is known to undergo change in linkage type in association with oncogenesis, and expected to be usable as a biomarker for cancers. Moreover, glycosylation is known to affect the effect of biopharmaceutical products, and hence analysis of the linkage type of sialic acid is also important in quality control of biopharmaceutical products.

However, analysis of a sialylated glycan including sialic acid through mass spectrometry is not easy because a negative charge possessed by the sialic acid suppresses ionization of the sialic acid in the positive ion mode and the sialic acid is easily decomposed. In addition, type-by-type analysis of the linkage type of sialic acid is more difficult because molecular weights are identical among sialic acids with different linkage types.

Chemical derivatization methods to modify in a linkage type-specific manner have been proposed for type-by-type analysis of the linkage type of sialic acid. In such chemical derivatization methods, which utilize the higher tendency of α2,3-sialic acid to undergo intramolecular dehydration by a dehydration condensation agent than that of α2,6-sialic acid, α2,3-sialic acid is lactonized through intramolecular dehydration and α2,6-sialic acid is simultaneously reacted with a nucleophilic agent such as alcohol or amine. Molecules then formed have different masses depending on the linkage type of the sialic acid, and hence the linkage type of sialic acid can be analyzed in a type-by-type manner through mass spectrometry.

However, a lactone of α2,3-sialic acid is unstable, and even begins to decompose on being dissolved in water, and a substantial fraction may decompose roughly in 48 hours. Hence, the lactone is conventionally stabilized through derivatization to prevent deterioration of the quantitativity associated with the decomposition of the lactone.

In PTL1 and NPTL1, a solution containing isopropylamine and a dehydration condensation agent is added to a free glycan to lactonize α2,3-sialic acid and amidate α2,6-sialic acid. Thereafter, for the purpose of hydrolyzing and amidating the lactone, a solution containing methylamine hydrochloride and a solution containing a dehydration condensation agent are added in the order presented to react for 2 hours.

In NPTL2, a solution containing dimethylamine and a dehydration condensation agent is added to glycoprotein on a tissue section to lactonize α2,3-sialic acid and amidate α2,6-sialic acid. Thereafter, for the purpose of hydrolyzing and amidating the lactone, aqueous ammonia is added to react for 2 hours, as illustrated in FIG. 1 (B) in NPTL2.

In NPTL3, a solution containing ethanol and a dehydration condensation agent is added to glycoprotein bonded to a solid phase carrier to lactonize α2,3-sialic acid and esterify α2,6-sialic acid. Thereafter, for the purpose of hydrolyzing the lactone, Tris buffer at pH 10 is added to the sample to react for 1 hour, and then a solution containing methylamine hydrochloride and a dehydration condensation agent is added to the sample to react for 30 minutes, as illustrated in Scheme 1 (b) in NPTL3.

CITATION LIST

Patent Literature

PTL1: Japanese Patent No. 6135710

Non-Patent Literature

NPTL1: Nishikaze T, Tsumoto H, Sekiya S, Iwamoto S, Miura Y, Tanaka K. "Differentiation of Sialyl Linkage Isomers by One-Pot Sialic Acid Derivatization for Mass Spectrometry-Based Glycan Profiling," Analytical Chemistry, (US), ACS Publications, Feb. 21, 2017, Volume 89, Issue 4, pp. 2353-2360

NPTL2: Hoist S, Heijs B, de Haan N, van Zeijl R J, Briaire-de Bruijn I H, van Pelt G W, Mehta A S, Angel P M, Mesker W E, Tollenaar R A, Drake R R, Bovee J V, McDonnell L A, Wuhrer M. "Linkage-Specific in Situ Sialic Acid Derivatization for N-Glycan Mass Spectrometry Imaging of Formalin-Fixed Paraffin-Embedded Tissues," Analytical Chemistry, (US), ACS Publications, Jun. 7, 2016, Volume 88, Issue 11, pp. 5904-5913

NPTL3: Li H, Gao W, Feng X, Liu B F, Liu X. "MALDI-MS analysis of sialylated N-glycan linkage isomers using solid-phase two step derivatization method," Analytica Chimica Acta, (the Netherlands), Elsevier B. V., Jun. 14, 2016, Volume 924, pp. 77-85

SUMMARY OF INVENTION

Technical Problem

Each of the methods of the prior art literatures intends to induce ring-opening of the lactone through hydrolysis and then react the carboxy group generated through the ring-opening with amine in the presence of a dehydration condensation agent. Therefore, a long time and complicated operations are required for the reaction.

Solution to Problem

According to the 1st aspect of the present invention, a method for preparing a sample comprising a glycan comprises: performing a lactonization reaction in which at least a part of sialic acids included in the glycan is lactonized; and performing an amidation reaction in which lactones of lactonized sialic acids are amidated through addition of an amidation reaction solution to the sample, the amidation reaction solution comprising at least one selected from the group consisting of ammonia, an amine, and a salt thereof that is reacted with the lactonized sialic acids.

According to the 2nd aspect of the present invention, it is preferred that the method for preparing a sample according to the 1st aspect further comprises: performing an operation that causes a lactonization reaction solution used for the lactonization reaction to be removed from the sample after the lactonization reaction.

According to the 3rd aspect of the present invention, in the method for preparing a sample according to the 1st or 2nd aspect, it is preferred that only contacting the sample with the amidation reaction solution is performed for the amidation reaction.

According to the 4th aspect of the present invention, in the method for preparing a sample according to any one of the 1st to 3rd aspects, it is preferred that the amidation reaction solution does not include a dehydration condensation agent that is reacted with the lactones.

According to the 5th aspect of the present invention, in the method for preparing a sample according to any one of the 1st to 4th aspects, it is preferred that an operation that reacts the sample with a dehydration condensation agent is not performed after the addition of the amidation reaction solution to the sample.

According to the 6th aspect of the present invention, in the method for preparing a sample according to any one of the 1st to 5th aspects, it is preferred that a time during which the sample is in contact with the amidation reaction solution for the amidation reaction is shorter than 30 minutes.

According to the 7th aspect of the present invention, in the method for preparing a sample according to any one of the 1st to 6th aspects, it is preferred that the amine is a primary amine.

According to the 8th aspect of the present invention, in the method for preparing a sample according to any one of the 1st to 7th aspects, it is preferred that the amine includes an alkyl group.

According to the 9th aspect of the present invention, in the method for preparing a sample according to 8th aspect, it is preferred that the alkyl group is unbranched.

According to the 10th aspect of the present invention, in the method for preparing a sample according to any one of the 1st to 9th aspects, it is preferred that the amine includes at least one of an allyl group and a hydroxy group.

According to the 11th aspect of the present invention, in the method for preparing a sample according to any one of the 1st to 10th aspects, it is preferred that pH of the amidation reaction solution is 8.0 or higher.

According to the 12th aspect of the present invention, in the method for preparing a sample according to any one of the 1st to 11th aspects, it is preferred that in the lactonization reaction, at least a part of the sialic acids is lactonized through addition of a lactonization reaction solution to the sample, the lactonization reaction solution comprising a dehydration condensation agent that is reacted with the sialic acids included in the glycan.

According to the 13th aspect of the present invention, in the method for preparing a sample according to 12th aspect, it is preferred that the lactonization reaction solution further comprises a nucleophilic agent that is reacted with the sialic acids included in the glycan; the nucleophilic agent differs in mass from the ammonia or the amine used in the amidation reaction; and a part of the sialic acids is lactonized based on the linkage type of the sialic acid through addition of the lactonization reaction solution to the sample, and at least a part of the nucleophilic agent is linked to another part of the sialic acids.

According to the 14th aspect of the present invention, in the method for preparing a sample according to any one of the 1st to 13th aspects, it is preferred that in the lactonization reaction, at least one selected from the group consisting of α2,3-sialic acid, α2,8-sialic acid, and α2,9-sialic acid among the sialic acids is lactonized.

According to the 15th aspect of the present invention, in the method for preparing a sample according to 13th aspect, it is preferred that α2,3-sialic acid is lactonized and α2,6-sialic acid is linked to a part of the nucleophilic agent through addition of the lactonization reaction solution to the sample.

According to the 16th aspect of the present invention, in the method for preparing a sample according to any one of the 1st to 15th aspects, it is preferred that the sample is contacted with the amidation reaction solution in a state in which the sample is bonded to or adsorbed on a solid phase carrier.

According to the 17th aspect of the present invention, in the method for preparing a sample according to any one of the 1st to 16th aspects, it is preferred that a solvent of the amidation reaction solution comprises an organic solvent.

According to the 18th aspect of the present invention, an analysis method comprises: preparing a sample by using the method for preparing a sample according to any one of the 1st to 17th aspects; and analyzing the prepared sample.

According to the 19th aspect of the present invention, in the analysis method according to 18th aspect, it is preferred that the prepared sample is analyzed through at least one of mass spectrometry and chromatography.

Advantageous Effects of Invention

The present invention enables quicker stabilization of a lactonized part in a glycan.

DESCRIPTION OF EMBODIMENTS

Hereinafter, embodiments of the present invention will be described with reference to the drawings. The present inventors have found that quick amidation can be caused through addition of an amidation reaction solution to a sample including a lactonized sialic acid, and this amidation reaction solution contains at least one compound selected from the group consisting of ammonia, an amine, and a salt thereof that is reacted with the lactonized sialic acid.

Figure 1:
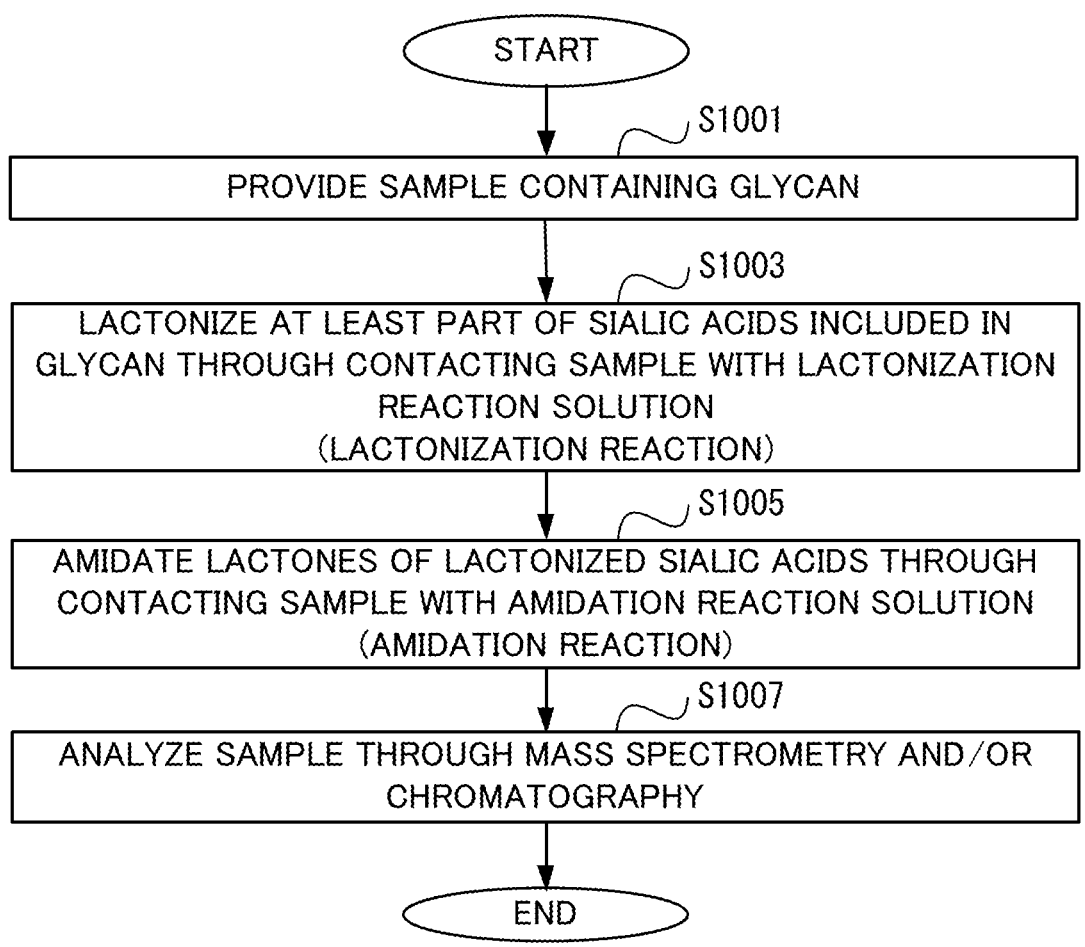
FIG. 1 shows a flowchart illustrating the procedure of an analysis method according to one embodiment.

FIG. 1 shows a flowchart illustrating the procedure of an analysis method according to the method for preparing a sample in the present embodiment. In a step S1001, a sample containing a glycan is provided.

The sample containing a glycan is not particularly limited, and can contain at least one molecule selected from the group consisting of a free glycan, a glycopeptide and a glycoprotein, and a glycolipid. The method for preparing a sample according to the present embodiment is used for modification of a lactone formed in a glycan, and in particular suitably used for analysis of the linkage type of sialic acid. Hence, it is preferable for the sample to contain a glycan which may have a sialic acid at an end thereof such as a N-linked glycan, an O-linked glycan, or a glycolipid-type glycan. It is preferable for the glycan in the sample to include at least one of α2,3-sialic acid, α2,8-sialic acid, and α2,9-sialic acid.

If a sample containing a free glycan is used, the glycan can be a glycan released from a glycoprotein or a glycopeptide, or a glycolipid. To release a glycan from a glycoprotein or a glycopeptide, or a glycolipid, enzymatic treatment with an enzyme such as N-glycosidase, O-glycosidase, endoglycoceramidase or the like, hydrazinolysis, or β-elimination by alkali treatment, or the like can be used. In releasing an N-linked glycan from a peptide chain of a glycopeptide or a glycoprotein, enzymatic treatment with an enzyme such as peptide-N-glycosidase F (PNGase F), peptide-N-glycosidase A (PNGase A), or endo-β-N-acetylglucosaminidase (Endo M) is suitably used. Alternatively, modification such as pyridylamination (PA labeling) can be appropriately performed for a reducing end of the glycan. Cleavage of the peptide chain of a glycopeptide or a glycoprotein, which is described later, may be performed before the enzyme treatment.

If the sample contains a glycopeptide and/or a glycoprotein, treatment to suppress a side reaction of the peptide moiety can be appropriately performed, as described later in the section "Suppression of Side Reaction of Glycopeptide and Glycoprotein." In the case that the peptide chain of a glycopeptide or a glycoprotein includes a large number of amino acid residues, it is preferable to cleave the peptide chain in use through enzymatic cleavage or the like. In preparing a sample for mass spectrometry, for example, the number of amino acid residues in the peptide chain is preferably 30 or less, more preferably 20 or less, and even more preferably 15 or less. In the case that the origin of the peptide to which a glycan is linked is needed to be clarified, the number of amino acid residues in the peptide chain is preferably two or more, and more preferably three or more.

A digestive enzyme is used in cleaving the peptide chain of a glycopeptide or a glycoprotein, and examples thereof include trypsin, Lys-C, arginine endopeptidase, chymotrypsin, pepsin, thermolysin, proteinase K, and pronase E. Two or more of these digestive enzymes may be used in combination. Conditions for cleavage of the peptide chain are not particularly limited, and a protocol suitable for the digestive enzyme to be used is appropriately employed. Before this cleavage, denaturation treatment or alkylation treatment may be performed for a protein or a peptide in the sample. Conditions for the denaturation treatment or the alkylation treatment are not particularly limited.

It is to be noted that the cleavage treatment for the peptide chain may be performed after the lactone included in the glycan is amidated through the method for preparing a sample according to the present embodiment. The cleavage of the peptide chain may be achieved not through enzymatic cleavage but through chemical cleavage or any other method.

The completion of the step S1001 is followed by a step S1003.

Lactonization Reaction

In the step S1003, a lactonization reaction is performed (hereinafter, the expression "lactonization reaction" refers to the lactonization reaction in the step S1003, unless otherwise stated) in which at least a part of sialic acids included in the glycan is lactonized through contacting the sample with a reaction solution for lactonization (hereinafter, referred to as "lactonization reaction solution"). In the lactonization reaction, α2,3-sialic acid, α2,8-sialic acid, and α2,9-sialic acid are suitably lactonized. The lactonization reaction solution contains a dehydration condensation agent.

In the following, type-by-type analysis of the linkage type of sialic acid will be described as an example. In this case, the lactonization reaction solution contains a nucleophilic agent containing at least one selected from the group consisting of an alcohol, an amine, and a salt thereof, in addition to the dehydration condensation agent.

The types and concentrations of the dehydration condensation agent and the nucleophilic agent are adjusted to selectively cause a dehydration reaction or a nucleophilic reaction based on the linkage type of sialic acid. A lactone generated through intramolecular dehydration of the carboxy group of α2,3-sialic acid is a six-membered ring, and a lactone generated through intramolecular dehydration of the carboxy group of α2,6-sialic acid is to be a seven-membered ring. Six-membered rings are more stable than seven-membered rings, and thus α2,3-sialic acid, which generates a six-membered ring, has a higher tendency to be lactonized than that of α2,6-sialic acid. Also, the carboxy group of α2,3-sialic acid is present at a position causing relatively high steric hindrance as compared with the carboxy group of α2,6-sialic acid, and hence α2,3-sialic acid is less reactive with a large molecule than α2,6-sialic acid. Based on such differences in molecular structure among the linkage types of sialic acid, the types and concentrations of the dehydration condensation agent and the nucleophilic agent are adjusted to provide different modifications for different linkage types of sialic acids.

Dehydration Condensation Agent in Lactonization Reaction

It is preferable for the dehydration condensation agent to contain a carbodiimide. This is because when a carbodiimide is used, the carboxy group present at a site causing high steric hindrance is less likely to be amidated than in use of a phosphonium-based dehydration condensation agent (what is called BOP reagent) or an uronium-based dehydration condensation agent as the dehydration condensation agent. Examples of the carbodiimide include N,N'-dicyclohexyl-carbodiimide (DCC), N-(3-dimethylaminopropyl)-N'-ethyl-carbodiimide (EDC), N,N'-diisopropylcarbodiimide (DIC), 1-tert-butyl-3-ethylcarbodiimide (BEC), N,N'-di-tert-butyl-carbodiimide, 1,3-di-p-tolylcarbodiimide, bis(2,6-diisopropylphenyl)carbodiimide, bis(trimethylsilyl)carbodiimide, and 1,3-bis(2,2-dimethyl-1,3-dioxolan-4-ylmethyl)carbodiimide(BDDC), and salts thereof Additive in Lactonization Reaction To promote dehydration condensation by the dehydration condensation agent and suppress a side reaction, a highly nucleophilic additive is preferably used in addition to the carbodiimide. Preferred examples of the highly nucleophilic additive for use include 1-hydroxybenzotriazole (HOBt), 1-hydroxy-7-aza-benzotriazole (HOAt), 4-(dimethylamino) pyridine (DMAP), ethyl 2-cyano-2-(hydroxyimino)acetate (CHA), N-hydroxy-succinimide (HOSu), 6-chloro-1-hydroxy-benzotriazole (Cl-HOBt), and N-hydroxy-3,4-dihydro-4-oxo-1,2,3-benzotriazine (HOOBt).

Nucleophilic Agent in Lactonization Reaction

The amine for use as the nucleophilic agent preferably contains primary and/or secondary alkylamine(s) having two or more carbon atoms. Preferred examples of the primary alkylamine include ethylamine, propylamine, isopropylamine, butylamine, sec-butylamine, and tert-butylamine. Preferred examples of the secondary alkylamine include dimethylamine, ethylmethylamine, diethylamine, propylmethylamine, and isopropylmethylamine. To lower the probability of the occurrence of amidation of a carboxy group present at a site with high steric hindrance such as the carboxy group of α2,3-sialic acid, use of an amine having a branched alkyl group such as isopropylamine is preferred. If an amine is used as the nucleophilic agent in the lactonization reaction solution, the carboxy group of a part of sialic acids such as α2,6-sialic acid is amidated based on the linkage type of the sialic acid.

The alcohol for use as the nucleophilic agent is not particularly limited, and methanol, ethanol, or the like can be used. If an alcohol is used as the nucleophilic agent in the lactonization reaction solution, the carboxy group of a part of sialic acids such as α2,6-sialic acid is esterified based on the linkage type of the sialic acid.

The nucleophilic agent may contain a salt of any of the above nucleophilic agents.

Phase for Lactonization Reaction

The lactonization reaction can be performed in any of a liquid phase and a solid phase. If the reaction is performed in a liquid phase, the reaction is preferably performed in a non-aqueous solvent such as dimethylsulfoxide (DMSO) or dimethylformamide (DMF). If the reaction is performed in a non-aqueous solvent, a side reaction is likely to be suppressed, which is suitable in use of a glycopeptide or a glycoprotein as a sample. The concentration of each component in the liquid phase reaction is not particularly limited, and can be appropriately determined according to the type or other factors of the dehydration condensation agent or the amine. For example, the concentration of the dehydration condensation agent in the lactonization reaction solution is preferably 1 mM to 5 M, and more preferably 10 mM to 3 M. If a carbodiimide and a highly nucleophilic additive such as HOAt or HOBt are used in combination, the concentration of each is preferably in the above range. The concentration of the amine in the lactonization reaction solution is preferably 0.01 to 20 M, and more preferably 0.1 M to 10 M. The reaction temperature during the lactonization reaction is preferably around −20° C. to 100° C., and more preferably −10° C. to 50° C.

If the lactonization reaction is performed in a solid phase, the solid phase carrier is not particularly limited as long as the solid phase carrier is capable of immobilizing a glycan, a glycopeptide, a glycoprotein, or the like. To immobilize a glycopeptide or a glycoprotein, for example, a solid phase carrier having, as a ligand, an epoxy group, a tosyl group, a carboxy group, an amino group, or the like can be used. To immobilize a glycan a solid phase carrier having, as a ligand, a hydrazide group or an aminooxy group, or the like can be used. Performing the reaction in a state in which the sample is immobilized to a solid phase carrier facilitates removal of the lactonization reaction solution after the lactonization reaction.

The completion of the step S1003 is followed by a step S1005.

It is preferable to perform an operation to remove the lactonization reaction solution from the sample after the lactonization reaction. The operation to remove the lactonization reaction solution is not particularly limited and any operation which sufficiently lowers the concentrations of components necessary for the lactonization reaction can be performed as appropriate, and examples thereof include: separation of the reaction solution from the glycan bonded to the solid phase carrier through centrifugation or the like followed by washing with a washing solution; and evaporation of the sample to dryness through centrifugal concentration.

Amidation Reaction

In the step S1005, an amidation reaction is performed (hereinafter, the expression "amidation reaction" refers to the amidation reaction in the step S1005, unless otherwise stated) in which lactones of the lactonized sialic acids are amidated through contacting the sample with a reaction solution for amidation of lactone (hereinafter, referred to as "amidation reaction solution"). The present inventors have found a method for directly and quickly amidating a lactone, which is quite contrast to the common technical knowledge of ring-opening of the lactone through hydrolysis followed by amidation of the carboxy group. The reaction of this method is different from hydrolysis since the reaction suitably proceeds even under anhydrous conditions as described later, and inferred to be aminolysis based on the interaction between an amino group and a lactone. Hereinafter, ring-opening and amidation of a lactone with ammonia, amine, or a salt thereof, available even under anhydrous conditions, is referred to as "aminolysis."

The amidation reaction solution contains at least one selected from the group consisting of ammonia, an amine, and a salt thereof. In use of an amine, the amine is another amine different from the amine used for the lactonization reaction solution, or the same amine the mass of which has been changed through modification with a stable isotope or the like. The amidation reaction does not require any dehydration condensation agent, and may be free of a dehydration condensation agent. Preferably, only contacting the sample with the amidation reaction solution is performed for the amidation reaction.

Although the amidation reaction does not require any dehydration condensation agent, the amidation reaction solution may contain a dehydration condensation agent. For example, the amidation reaction solution may be prepared by adding ammonia, an amine, or a salt thereof without removing the lactonization reaction solution that has been added to the sample in the step S1003. Thus, the lactone can be stabilized through a simple operation in the amidation reaction.

Amine in Amidation Reaction

The amine contained in the amidation reaction solution is preferably a primary amine, more preferably a primary amine having a linear hydrocarbon group, and even more preferably a primary amine having a linear alkyl group. The primary amine having a linear alkyl group as the amine contained in the amidation reaction solution is preferably a primary amine having 10 or less carbon atoms, more preferably a primary amine having seven or less carbon atoms, even more preferably methylamine, ethylamine, propylamine, butylamine, or pentylamine, and the most preferably methylamine. It is preferable for the amine contained in the amidation reaction solution to have a linear structure without any branch (hereinafter, "branch" refers to branch of a hydrocarbon chain), or have a smaller number of carbon atoms, because the lactone is more efficiently amidated.

If the amine contained in the amidation reaction solution is a primary amine having an unsaturated chain hydrocarbon group, the unsaturated chain hydrocarbon group preferably includes a double bond, and more preferably includes an allyl group, and the amine is the most preferably allylamine. The amine contained in the amidation reaction solution may be a primary amine including a hydroxy group, and in this case the amine is preferably ethanolamine. Although an example in which the amine contained in the amidation reaction solution includes an allyl group or a hydroxy group are presented in Examples described later, the amine contained in the amidation reaction solution is not particularly limited thereto, and may include various functional groups other than alkyl groups. When a glycan is modified and provided with such a functional group as a result of the amidation reaction, the modified glycan can be separated more easily not only through mass spectrometry but also through chromatography or the like.

The amidation reaction solution may contain a salt of any of the above amine.

Concentration of Amidation Reaction Solution

The concentration of ammonia, an amine, or a salt thereof in the amidation reaction solution is preferably 0.1 M (M denotes mol/L) or more, more preferably 0.3 M or more, even more preferably 0.5 M or more, further preferably 1.0 M or more, and the most preferably 3.0 M or more. In a preferred example, the amidation reaction solution contains ammonia or a primary amine, in particular, methylamine, and the concentration of the ammonia or a primary amine such as methylamine is preferably 0.1 M or more, more preferably 0.3 M or more, even more preferably 0.5 M or more, further preferably 1.0 M or more, and the most preferably 3.0 M or more. The higher the concentration of the amidation reaction solution is, the more reliably the lactone can be amidated.

Solvent of Amidation Reaction Solution

The solvent of the amidation reaction solution may be an aqueous solvent or an organic solvent. However, it is preferable for the solvent to have a lower water content in order to prevent hydrolysis of the lactone and cause amidation quickly and reliably. The solvent of the amidation reaction solution is preferably a dehydrated solvent, which has been subjected to a dehydration operation to reduce the water content, and more preferably an anhydrous solvent. The solvent of the amidation reaction solution preferably contains at least one of methanol and acetonitrile.

It is to be noted that the amidation reaction solution may contain a significant amount of water, and the solvent of the amidation reaction solution may be water.

pH of Amidation Reaction Solution

The pH of the amidation reaction solution is preferably 7.7 or higher, more preferably 8.0 or higher, even more preferably 8.8 or higher, and the most preferably 10.3 or higher. Higher pH is preferred for the amidation reaction solution because the lactone is more reliably amidated.

Time Needed for Amidation Reaction

The amidation reaction is completed within several seconds to several minutes. Thus, the time during which the sample is in contact with the amidation reaction solution for amidation of the lactone through the amidation reaction (hereinafter, referred to as "reaction time") is preferably shorter than 1 hour, more preferably shorter than 30 minutes, even more preferably shorter than 15 minutes, further preferably shorter than 5 minutes, and the most preferably shorter than 1 minute. Only washing the sample with the amidation reaction solution, or only temporarily passing the amidation reaction solution through the sample held on a carrier or the like is also suitable. The time from an end of contacting the sample with the lactonization reaction solution to an end of contacting the sample with the amidation reaction solution is preferably shorter than 1.5 hours, more preferably shorter than 1 hour, and even more preferably shorter than 30 minutes. Since the amidation reaction is completed within a short time in this way, deterioration of the quantitativity due to the decomposition of the lactone, which is unstable, can be prevented in analysis of the glycan. Through setting the reaction time of the amidation reaction to be short, analysis of the sample becomes more efficient.

State of Sample in Amidation Reaction

The amidation reaction can be performed in any of a liquid phase and a solid phase. The state of the sample in the amidation reaction is not particularly limited as long as the state allows contact between the sample and the amidation reaction solution. However, it is preferable to contact the sample with the amidation reaction solution in a state in which the glycan contained in the sample is bonded to or adsorbed on a solid phase carrier.

If the reaction is performed in a solid phase, the solid phase carrier for use is not particularly limited, as with the case of the lactonization reaction, as long as the solid phase carrier is capable of immobilizing a glycan, a glycopeptide, a glycoprotein, or the like. To immobilize a glycopeptide or a glycoprotein, for example, a solid phase carrier having, as a ligand, an epoxy group, a tosyl group, a carboxy group, an amino group, or the like can be used. To immobilize a glycan a solid phase carrier having, as a ligand, a hydrazide group or an aminooxy group, or the like can be used. From the viewpoint of ionization efficiency after the amidation, or the like, it is also preferable to allow the glycan to be adsorbed on a carrier or, in other words, a stationary phase for hydrophilic interaction chromatography (hereinafter, referred to as "HILIC"), and it is more preferable that this carrier for HILIC includes an amide group.

After the sample is immobilized to the solid phase carrier and subjected to the action of the amidation reaction solution for amidation, the sample can be suitably liberated from a carrier, for example, through a chemical technique or enzyme reaction and collected. For example, a glycoprotein or a glycopeptide immobilized to the carrier may be enzymatically cleaved and collected by using a glycosidase such as PNGase F or a digestive enzyme such as trypsin, and a glycan bonding to a solid phase carrier having a hydrazide group may be liberated and collected by using a weakly acidic solution. In HILIC, the sample can be collected through an amidation reaction with an amidation reaction solution containing acetonitrile or the like as a solvent followed by elution with an aqueous solution such as water.

Reacting in a state in which the sample is immobilized to a solid phase carrier facilitates removal of the reaction solution and desalting and purification, and thus sample preparation can be simplified. In use of a solid phase carrier, the sample is immobilized as the form of glycoprotein or glycopeptide and subjected to the amidation reaction, and then cleaved with a glycosidase such as PNGase F. Thereby, the sample after the amidation reaction can be collected as a free glycan.

The lactonized sample may be purified through HILIC and eluted, and then subjected to the amidation reaction. It is preferable to appropriately adjust the solvent for washing of the carrier for HILIC to lower the probability of the occurrence of hydrolysis.

As demonstrated in Examples as a preferred example of the method for preparing a sample in the present embodiment, the present inventors have found that aminolysis occurs for a glycan adsorbed on a solid phase carrier.

If the glycan in the sample includes α2,3-, α2,8-, and α2,9-sialic acids, in the above-described preparation method, each sialic acid is lactonized through the lactonization reaction in the step S1003, and the lactonized sialic acids are amidated to be stabilized through the amidation reaction in the step S1005.

The completion of the step S1005 is followed by a step S1007.

In the step S1007, the sample is analyzed through mass spectrometry and/or chromatography. The above-described lactonization reaction and amidation reaction result in a difference in mass between a glycan including a sialic acid less likely to be lactonized such as α2,6-sialic acid and a glycan including a sialic acid likely to be lactonized such as α2,3-sialic acid, α2,8-sialic acid, or α2,9-sialic acid. Therefore, these glycan can be separated through mass spectrometry based on the linkage type of sialic acid.

The ionization method in the mass spectrometry is not particularly limited, and matrix-assisted laser desorption ionization (MALDI), electrospray ionization (ESI), nano-electrospray ionization (nano-ESI), or the like can be used. MALDI is particularly preferred for the ionization method. In ionization in the mass spectrometry, either of the positive ion mode or the negative ion mode may be used. The mass spectrometry may be performed in multiple stages, which allows analysis of the structure of a glycan in addition to the linkage type of sialic acid, or the structure of a peptide chain.

Analysis may be performed by using an analysis method other than mass spectrometry, such as chromatography, based on the properties of a modified product resulting from the lactonization reaction and the amidation reaction. The column used for liquid chromatography is not particularly limited, and a hydrophobic reverse phase column such as C30, C18, C8, or C4, a carbon column, a normal phase column for HILIC, or any other column can be appropriately used. It is preferable for more precise analysis of components in the sample to make measurement by using mass spectrometry after liquid chromatography. In this case, it is more preferable to directly ionize the eluate from the liquid chromatograph with a mass spectrometer under online control.

At the completion of the step S1007, the procedure is terminated.

Suppression of Side Reaction of Glycopeptide and Glycoprotein

In the case that the lactonization reaction solution and the amidation reaction solution are added to a glycopeptide or a glycoprotein to modify sialic acids as described above, a side reaction may occur, such as intramolecular dehydration condensation between an amino group and a carboxy group present in the side chain of an amino acid or at an end of the main chain in the glycopeptide or the glycoprotein. In this case, a mass spectrum peak corresponding to a glycan to be analyzed is split, which disadvantageously complicates analysis.

The present inventors have revealed that the side reaction of a peptide moiety is primarily derived from the presence of an amino group, and that preliminary blocking of amino groups by using chemical modification, or the like, before modification of sialic acids can suppress the side reaction of a peptide moiety in modification of sialic acids. For the details, see the following literature: Takashi Nishikaze, Sadanori Sekiya, Shinichi Iwamoto, Koichi Tanaka. "A Universal Approach to linkage-Specific Derivatization for Sialic Acids on Glycopeptides," Journal of The American Society for Mass Spectrometry, June, 2017, Volume 28, Issue 1 Supplement, Poster No. MP091. Modification with the amidation reaction related to the present embodiment can be similarly applied to a glycopeptide and a glycoprotein. Specifically, a glycopeptide or a glycoprotein is subjected to a reaction to block amino groups such as dimethylamidation or guanidinylation, and then to the lactonization reaction followed by quick amidation via the amidation reaction. If a method for forming a lactone according to the linkage type of sialic acid is then used, the linkage type of sialic acid can be identified.

Some glycopeptides are less likely to undergo a side reaction by virtue of the properties based on the amino acid sequence. For example, a glycopeptide generated through digestion of the Fc region of IgG with a digestive enzyme such as trypsin does not include lysine, and an amino group at the N-terminal quickly undergoes cyclodehydration to be pyroglutamylated in the presence of a dehydration condensation agent. As a result, the amino groups are eliminated, and thus preliminary blocking of amino groups by dimethylamidation, guanidinylation, or the like is unnecessary. For such a glycopeptide, a mass spectrum sufficient for analysis can be acquired through the lactonization reaction without blocking of amino groups and amidation of the resulting lactone via the amidation reaction.

The present invention is not limited to the contents of the above embodiments. Other modes contemplated from the scope of the technical idea of the present invention are also included in the scope of the present invention.

EXAMPLES

Now, examples of the present embodiment will be presented. However, the present invention is not limited to the following Examples. Hereinafter, "%" denotes "% by weight" unless otherwise stated.

Examination on Amine Concentration in Amidation Reaction

A glycan was released from sialylglycopeptide (α2,3-SGP; Fushimi Pharmaceutical Co., Ltd.) including α2,3-sialic acid linked thereto with PNGase F, and used as a sample. The sialylglycopeptide was one in which a glycan was linked to a peptide of several residues. The sample was bonded to a solid phase carrier (BlotGlyco; Sumitomo Bakelite Co., Ltd.) consisting of beads having a hydrazide group as a ligand. The bonding of the glycan to the solid phase carrier was performed according to a standard protocol of the glycan purification kit BlotGlyco.

The carrier to which the glycan had been bonded was washed three times with 200 4 of DMSO. Thereafter, 100 4 of a lactonization reaction solution containing isopropylamine (2 M isopropylamine hydrochloride, 500 mM EDC-HCl, 500 mM HOBt) was added thereto, and reacted with mild stirring at 800 rpm for 1 hour. Through this operation, α2,6-sialic acid and α2,3-sialic acid were converted into isopropylamide and the lactone form, respectively. The reaction solution was removed through centrifugation, and washing was then performed once with 200 4 of methanol. Thereafter, the lactone was subjected to an amidation reaction through three times of washing with 200 4 of methylamine aqueous solution (concentration: 0.1% to 10%). Subsequently, washing was performed twice with 200 4 of methanol and three times with 200 4 of water. Thereafter, the glycan sample reacted was liberated from the carrier by using a method according to the standard protocol, and subjected to desalting and purification by using a Stage Tip Carbon followed by evaporation to dryness through centrifugal concentration (SpeedVac (Thermo Fisher Scientific)). The Stage Tip Carbon was a carbon column prepared by cutting an Empore Disk-Carbon (produced by 3M Company) into pieces having a diameter of approximately 1 mm and packing a 200 4 tip with the pieces. The sample subjected to evaporation to dryness was redissolved in 10 4 of water, and 1 μL was taken therefrom and dropped on a focus plate, and 0.5 4 of 100 mM 3AQ/CA and 2 mM ammonium sulfate dissolved in 50% acetonitrile (ACN), in which 3AQ/CA was used as a matrix, was added thereto, and the resultant was then reacted on a heat block at 75° C. for 1.5 hours for labeling of reducing ends of the glycan with 3AQ. After the completion of the reaction, the plate was cooled to room temperature, and time-of-flight mass spectrometry was performed through MALDI-QIT-TOF-MS (AXIMA-Resonance, Shimadzu/Kratos) in the negative ion mode.

Figure 2:
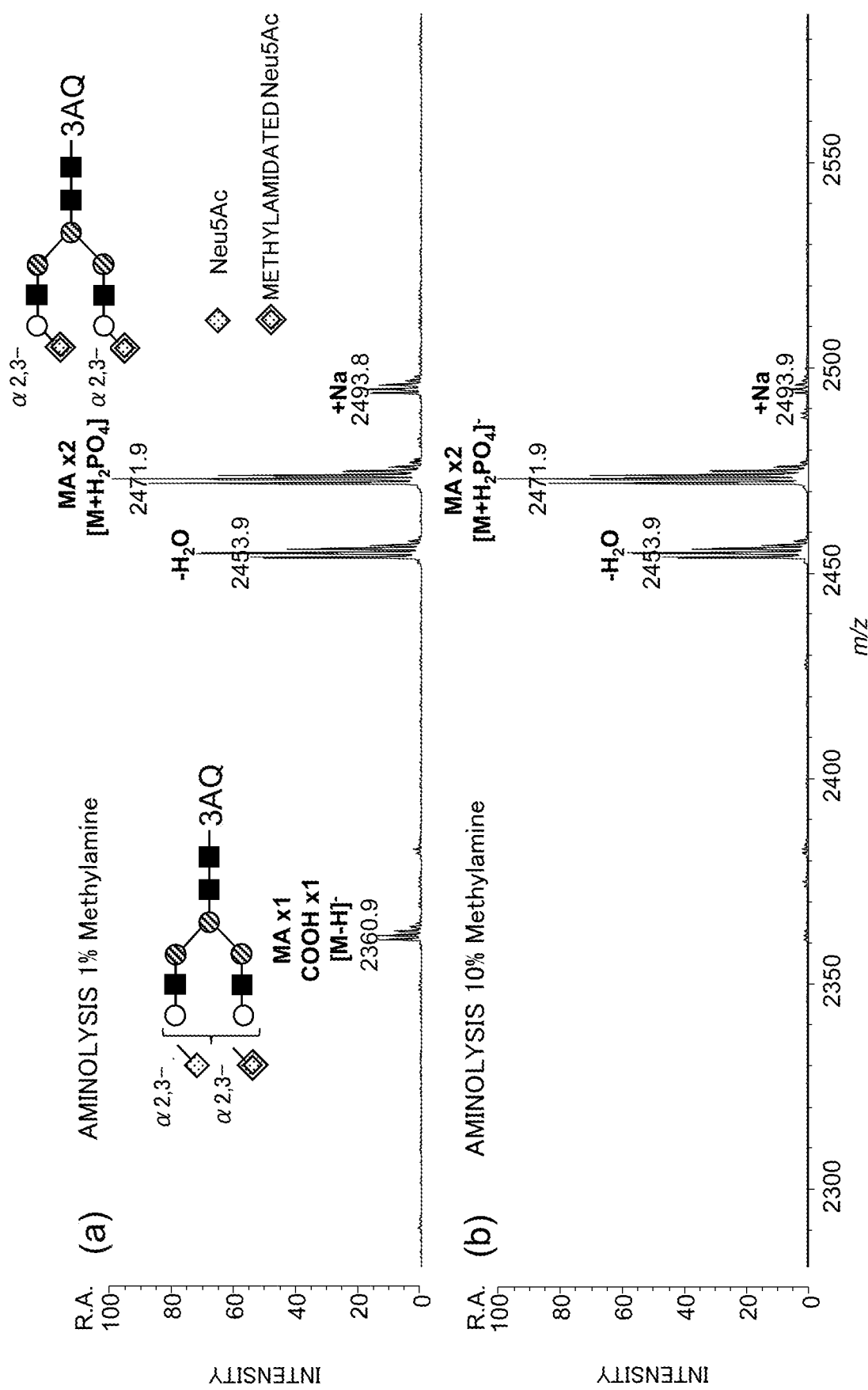
FIG. 2 shows mass spectra acquired in mass spectrometry in negative ion mode for reaction products obtained through a lactonization reaction and an amidation reaction of a glycan released from α2,3-sialylglycopeptide, where (a) shows a mass spectrum with a methylamine concentration of 1% in the amidation reaction, and (b) shows a mass spectrum with a methylamine concentration of 10% in the amidation reaction.

FIG. 2 shows mass spectra when aminolysis was caused by using (a) 1% or (b) 10% methylamine aqueous solution as the amidation reaction solution. The α2,3-A2-glycan released from α2,3-SGP as the sample had been subjected to intramolecular dehydration condensation with the above lactonization reaction solution for conversion into the lactone form. In this case, the hydrazide beads were then washed only with the methylamine solution without using any dehydration condensation agent. Nevertheless, it can be seen that the original lactone structure was methylamidated (corresponding to the peak at m/z 2471.9). The peak observed at m/z 2360.9 indicates one carboxy group left without being bonded to methylamine. This peak is inferred to correspond to a glycan which underwent not aminolysis but hydrolysis of a lactone. For the amidation reaction with 10% methylamine aqueous solution, this peak derived from hydrolysis was further weaker, indicating that aminolysis occurred in an almost exclusive manner.

Figure 3:
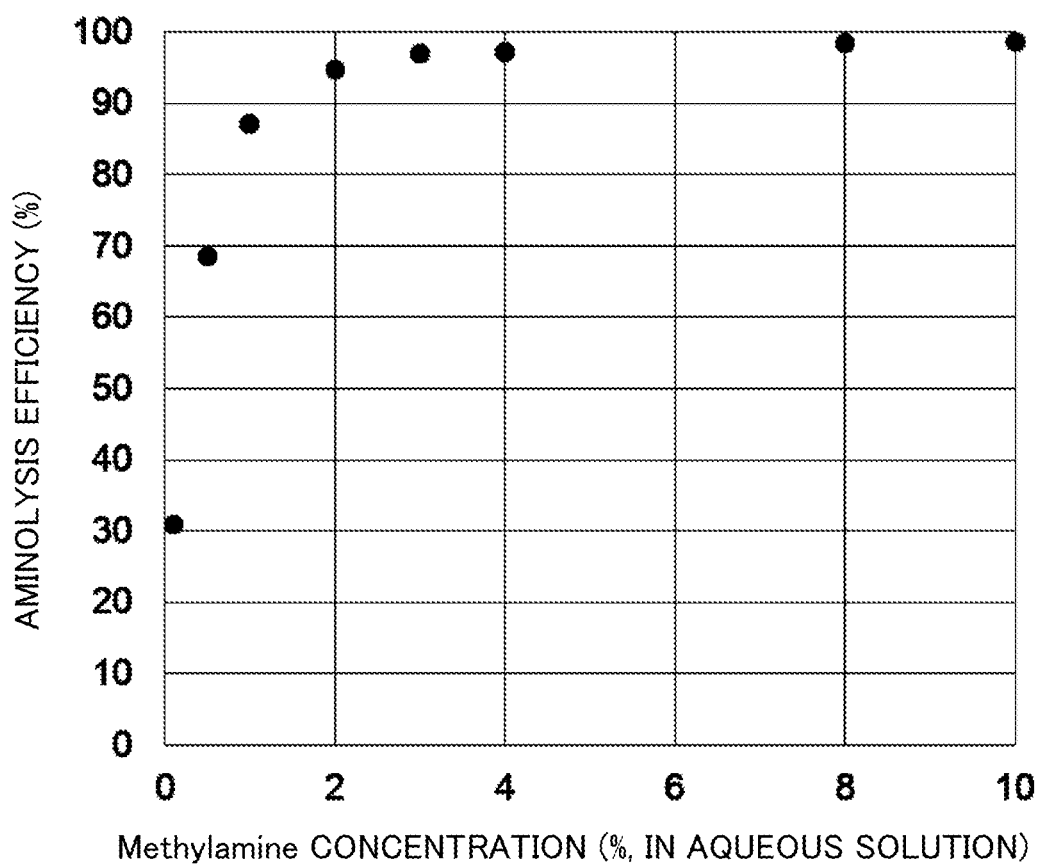
FIG. 3 shows a graph representing the relation between the concentration of methylamine aqueous solution and the efficiency of amidation in the amidation reaction.

FIG. 3 shows a graph representing ratios of sialic acids which underwent aminolysis in contrast to those which underwent hydrolysis (aminolysis efficiency) calculated from the peak signal intensities in the mass spectra against methylamine concentrations of the amidation reaction solution. Although aminolysis sufficiently occurred even when the concentration of methylamine solution was 1%, it can be seen that aminolysis was successfully caused in a more efficient manner with use of an amidation reaction solution containing a higher concentration of methylamine.

Examination on Type of Amine in Amidation Reaction

Figure 4:
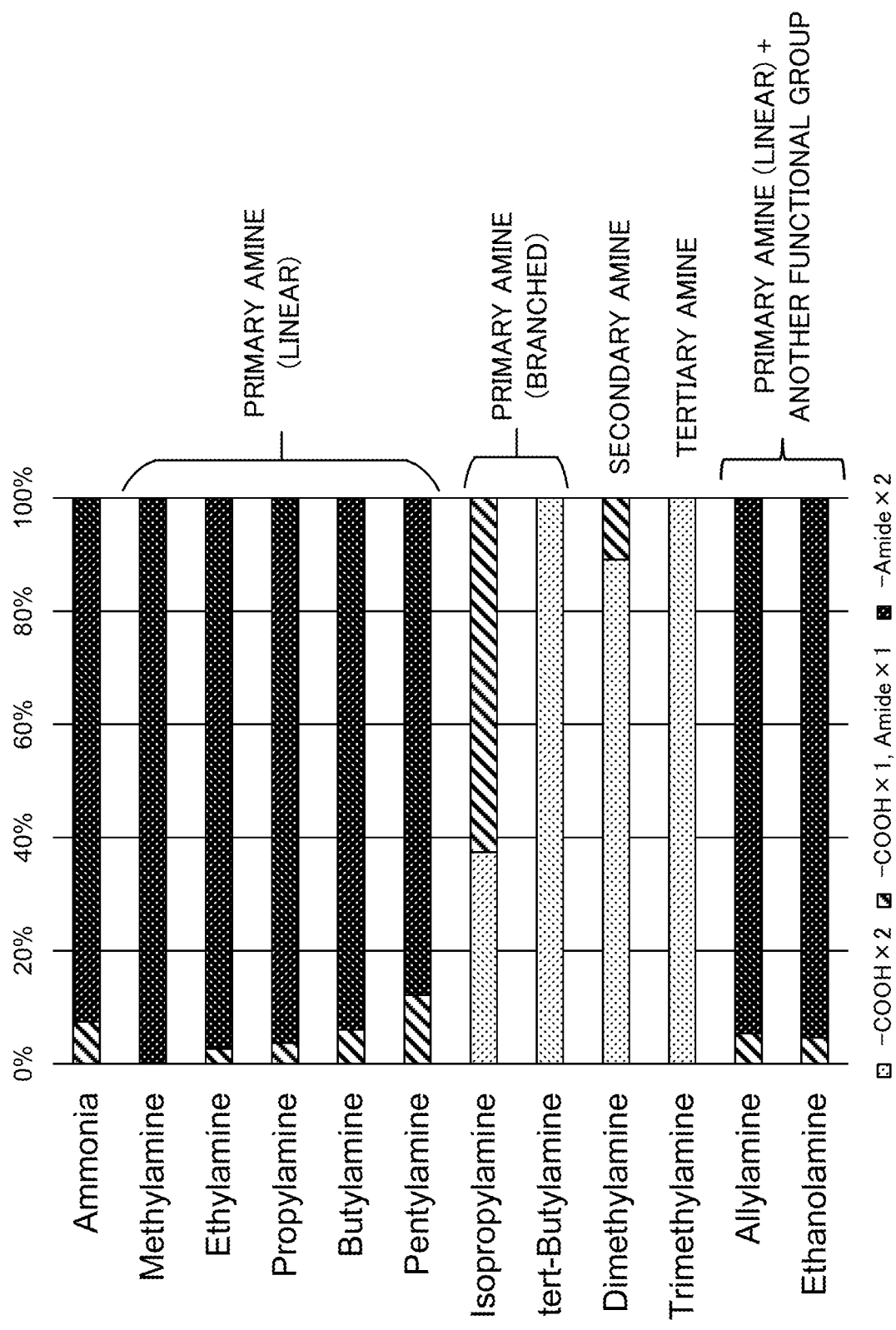
FIG. 4 shows graphs representing the types of amine in amidation reactions and respective production ratios of reaction products.

FIG. 4 shows graphs representing a production ratio in each amidation reaction with 3 M aqueous ammonia or an alkylamine aqueous solution (in a concentration corresponding to 10% for methylamine) as the amidation reaction solution under a condition generally identical to those in the above examination on the amine concentration.

The results in FIG. 4 show that while aminolysis was successfully caused in an efficient manner for ammonia and unbranched primary alkylamines, the aminolysis efficiency was low and hydrolysis (production of —COOH) was dominant for branched alkylamines including isopropylamine and tert-butylamine. When a tertiary amine was used for the amidation reaction solution, only hydrolysis occurred because the tertiary amine does not inherently react even in the presence of a dehydration condensation agent. Even when a secondary amine was used, the secondary amine did not react well, and hydrolysis dominantly occurred. For allylamine and ethanolamine, aminolysis dominantly occurred. These results revealed that any primary amine at least having no branch in the hydrocarbon chain is acceptable even if the primary amine includes another functional group, and a double bond or a hydroxy group may be included in the primary amine. Thus, it is understood that a primary amine having no branch in the carbon chain are particularly suitable for the occurrence of aminolysis.

Examination on Solvent in Amidation Reaction

Figure 5:
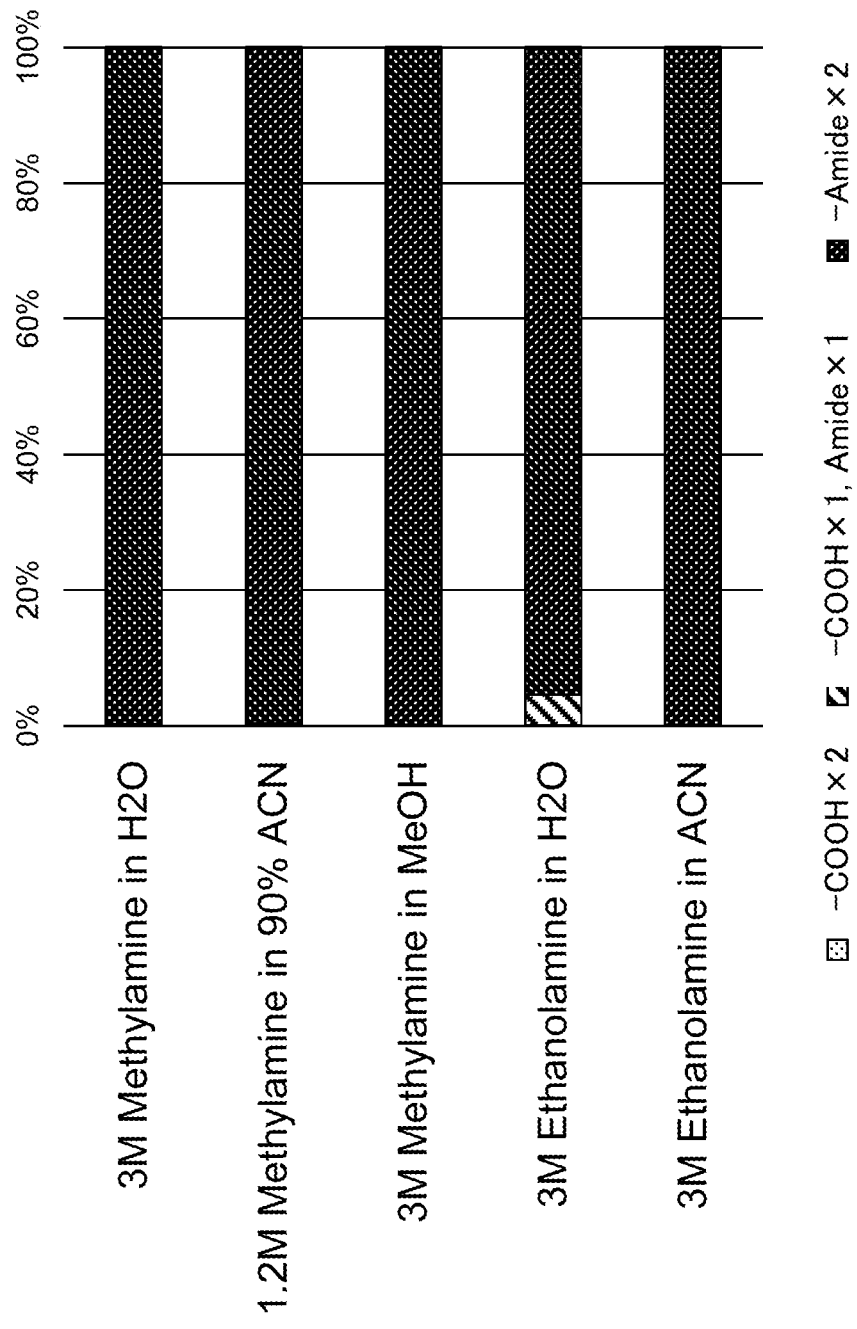
FIG. 5 shows graphs representing the types of amine and solvent in amidation reactions and respective production ratios of reaction products.

FIG. 5 shows graphs representing production ratios with 1.2 M methylamine dissolved in 90% ACN, 3 M methylamine dissolved in methanol, or 3 M ethanolamine dissolved in ACN, etc., as the amidation reaction solution, under conditions generally identical to those in the above examination.

The results in FIG. 5 show that aminolysis occurred with a high fraction for each case, and the peak corresponding to an amidated glycan was dominantly observed. Amidation occurred without any problem even when an amine dissolved in methanol or ACN substantially free of water was used, which strongly suggests that there occurred not amidation following temporary hydrolysis of a lactone but aminolysis to amidate by the direct action of amine on a lactone. Hydrolysis was more suppressed under conditions substantially free of water, and amidation occurred in an almost exclusive manner even when ethanolamine, which caused hydrolysis to around 5% of sialic acids in water solvent, was used for the amidation reaction solution.

Examination on pH in Amidation Reaction

Figure 6:
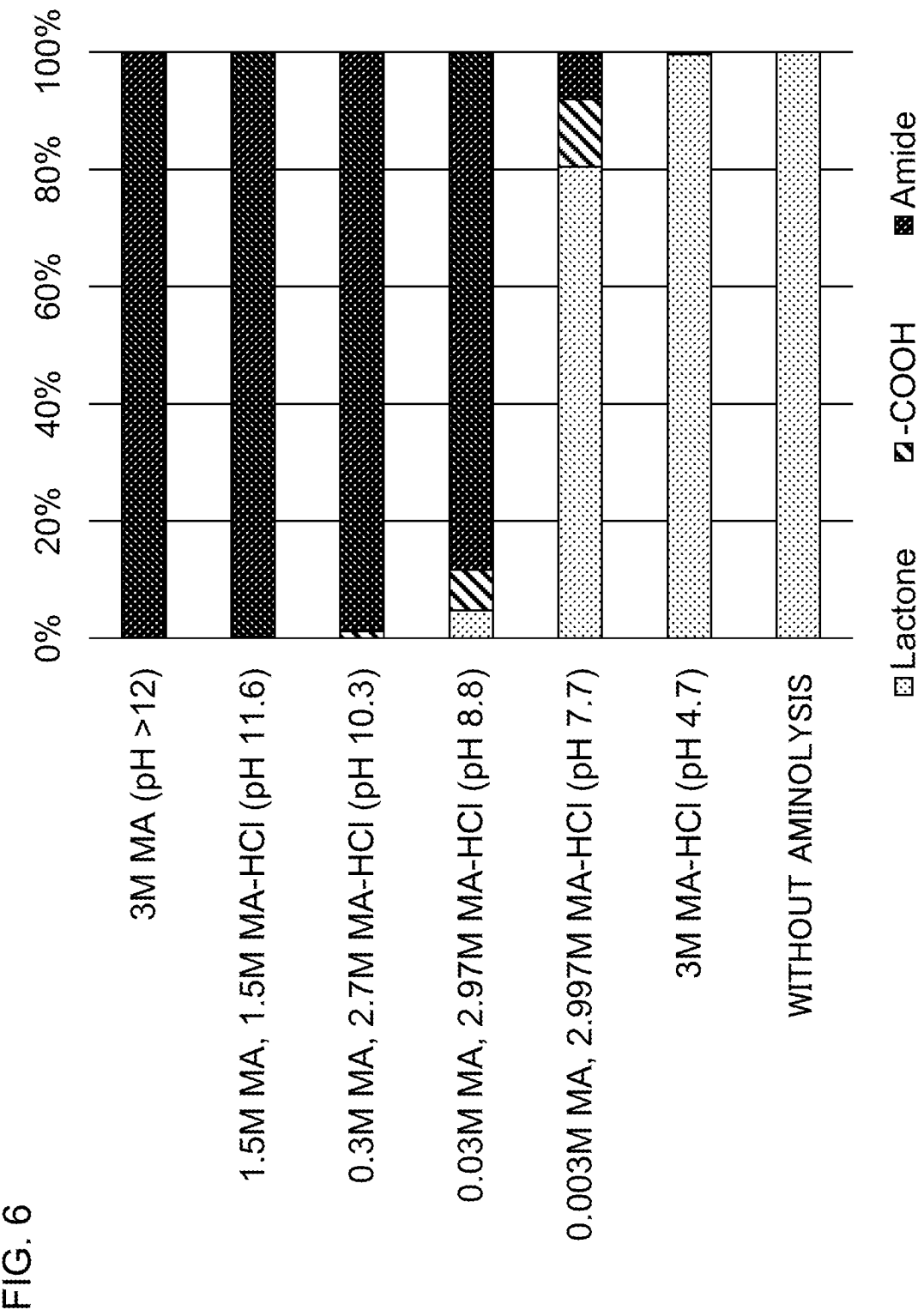
FIG. 6 shows graphs representing pH in amidation reactions and respective production ratios of reaction products.

FIG. 6 shows graphs representing production ratios with amidation reaction solutions prepared by mixing 3 M methylamine aqueous solution and 3 M methylamine hydrochloride aqueous solution at arbitrary ratios under conditions generally identical to those in the above examination. "MA" and "MA-HCl" in FIG. 6 represent methylamine aqueous solution and methylamine hydrochloride aqueous solution, respectively.

In the present examination, it was expected that α2,3-sialic acid would remain as a lactone even after addition of the amidation reaction solution to the sample under some conditions. Accordingly, to more quantitatively evaluate an unstable lactone, the amidation reaction solution was added to the sample for an amidation reaction, washing was then performed twice with 200 μL of $H_2O$ and twice with 200 μL of ACN, and another amidation reaction was subsequently performed with an amidation reaction solution containing 3 M ethanolamine dissolved in ACN. Under conditions for this two-step amidation reaction, amidated products of the first-step amidation reaction (detected as a methylamidated form), hydrolyzed products (detected as —COOH), and products remaining as lactones (detected as an amidated form with ethanolamine) can be clearly discriminated. The amidation reaction in the present examination was performed not through three cycles of washing performed in the above with 200 μL of the amidation reaction solution, but through adding 100 μL of the amidation reaction solution followed by stirring at 700 rpm for 2 minutes.

The results in FIG. 6 show that aminolysis hardly occurred when the amidation reaction solution was not added ("without aminolysis") or when 3 M methylamine hydrochloride solution (pH 4.7) was used as the amidation reaction solution, and substantially all the sialic acids were remaining as lactones. When the ratio of methylamine solution in preparing the amidation reaction solution was raised to increase pH, the sialic acids gradually underwent hydrolysis and aminolysis, and around 90% of the sialic acids were amidated at pH 8.8, and substantially all the sialic acids were amidated with an amidation reaction solution at pH 10.3 or higher.

Examination on Amidation Reaction Using Sample of Glycan Released from Fetuin

The glycoprotein fetuin was dissolved in 20 mM ammonium bicarbonate, 10 mM DTT, and 0.02% SDS, and treated at 100° C. for 3 minutes for denaturation and reduction. Thereafter, the resultant was cooled to room temperature, and PNGase F was added thereto, and was incubated at 37° C. overnight to release the glycan. The next day, the PNGase F was deactivated by heating at 100° C. for 3 minutes to terminate the enzyme reaction.

The released glycan was bonded to hydrazide beads and subjected to linkage type-specific modification with a lactonization reaction solution containing isopropylamine as in the above examination, and then subjected to an amidation reaction with 10% methylamine aqueous solution. Elution from the beads and detection by using mass spectrometry were performed as in the above examination.

Figure 7:
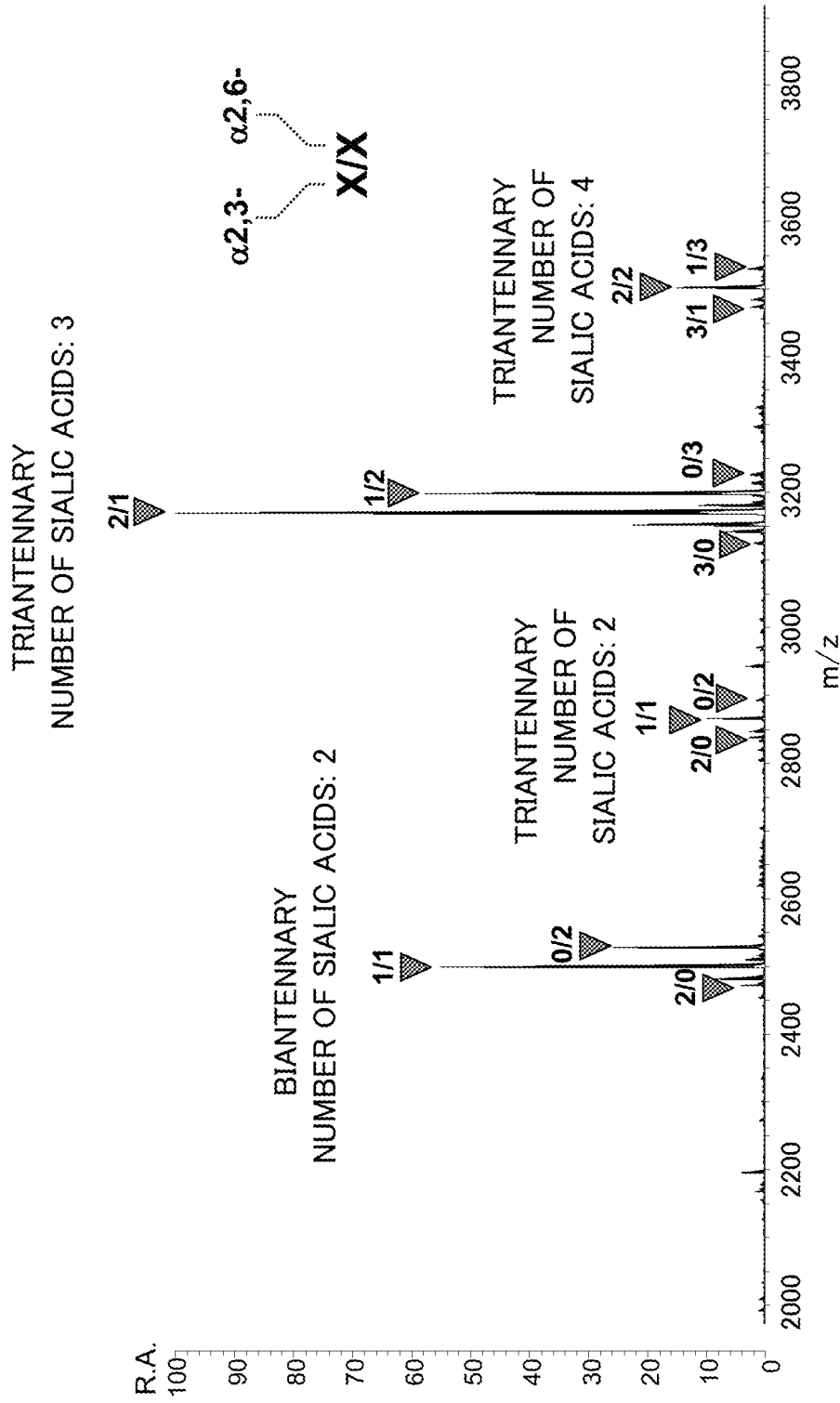
FIG. 7 shows a mass spectrum acquired in mass spectrometry for reaction products obtained through a lactonization reaction and an amidation reaction of a glycan released from the glycoprotein fetuin.

FIG. 7 shows a mass spectrum for the glycan released from fetuin. Among numerals at each peak, the left numeral denotes the number of α2,3-sialic acids included in the molecule corresponding to the peak, and the right numeral denotes the number of α2,6-sialic acids included in the same molecule. Neither a product of hydrolysis nor an unreacted form was detected, which indicates that lactonized sialic acids were efficiently methylamidated. Comparison between this mass spectrum and mass spectra reported in PTL 1 and NPTL1 teaches that the lactone was directly methylamidated through aminolysis in an efficient manner even without undergoing an amidation reaction with a dehydration condensation agent.

Examination on Amidation Reaction Using Sample of Glycolipid-Type Glycan

Human Disialogangliosides GD1a and GD1b (HyTest), which are glycosphingolipids, were used as samples. Each of the glycolipids was dissolved in 45 μL of 50 mM sodium acetate buffer (pH 5.5) containing 0.2% Triton x100, and left to stand with warming at 60° C. for 20 minutes, and 5 μL of Endoglycoceramidase I (purified from actinomycetes with reference to the following literature:
Ishibashi Y, Nakasone T, Kiyohara M, Horibata Y, Sakaguchi K, Hijikata A, Ichinose S, Omori A, Yasui Y, Imamura A, Ishida H, Kiso M, Okino N, and Ito M. "A novel endoglycoceramidase hydrolyzes oligogalactosylceramides to produce galactooligosaccharides and ceramides," Journal of Biological Chemistry, 2007, Volume 282, pp. 11386-11396) was then added thereto to perform glycan elimination reaction at 37° C. for 16 hours.

The released glycolipid-type glycan was bonded to a hydrazide carrier and subjected to capping for excessive hydrazide groups according to the BlotGlyco standard protocol as in the above examination, and then subjected to linkage type-specific modification of sialic acid with isopropylamine. Subsequently, washing was performed three times with 200 μL of 1% methylamine aqueous solution for an amidation reaction, and then the hydrazide carrier was washed three times with 200 μL of DMSO, three times with 200 μL of methanol, and three times with 200 μL of water. Thereafter, the glycan was labeled at reducing ends with the sensitizing reagent aoWR while being liberated from the carrier. Then, the excessive reagent was removed with an HILIC carrier, and the sample was ionized through MALDI using 2,5-dihydroxybenzoic acid (2,5-DHB) as a matrix, and a mass spectrum was acquired through time-of-flight mass spectrometry (MALDI-TOF MS) in the positive ion mode.

Figure 8:
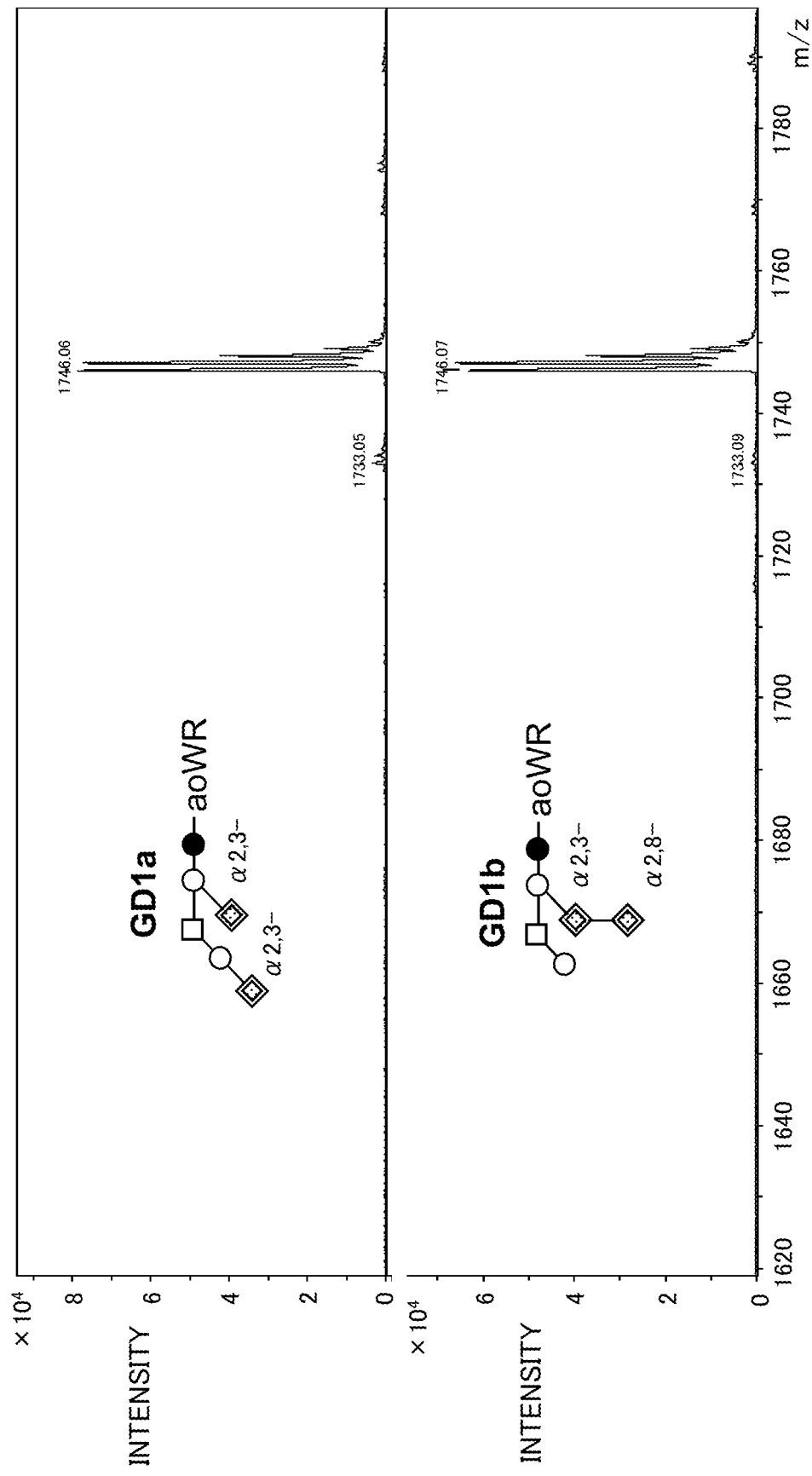
FIG. 8 shows mass spectra acquired in mass spectrometry for reaction products obtained through a lactonization reaction and an amidation reaction of a glycan released from disialoganglioside GD1a (top) and a glycan including α2,8-sialic acid released from disialoganglioside GD1b (bottom), where GD1a and GD1b are glycosphingolipids.

FIG. 8 shows obtained mass spectra for the glycolipid-type glycans. The top is a mass spectrum for the glycan released from the disialoganglioside GD1a, and the bottom is a mass spectrum for the glycan released from the disialoganglioside GD1b, in which GD1a and GD1b are glycosphingolipids. For the GD1a glycan, having two α2,3-sialic acids, a signal was observed at m/z 1746. This corresponds to the mass when both of the two α2,3-sialic acids were methylamidated. This result indicates that a glycolipid-type glycan is similarly methylamidated via lactonization in aminolysis. As with the case of the GD1a form, a signal was observed at m/z 1746 for the GD1b form, and two sialic acids were both methylamidated. The GD1b form has a linear polysialic acid structure including α2,3-sialic acid and α2,8-sialic acid linked to this α2,3-sialic acid, and both of the sialic acids were methylamidated. This result suggests that the aminolysis according to the present invention proceeds without any problem even for a lactone generated from α2,8-sialic acid.

Examination on Amidation Reaction on HILIC Carrier

α2,3-SGP was dissolved in 20 mM ammonium bicarbonate, and PNGase F was added thereto, and the resultant was incubated at 37° C. overnight to release the glycan. The next day, the PNGase F was deactivated by heating at 100° C. for 3 minutes to terminate the enzyme reaction. Thereafter, the resultant was desalted with a Stage Tip Carbon, and subjected to evaporation to dryness in an Eppendorf tube by using a SpeedVac.

Thereafter, 20 μL of a lactonization reaction solution containing isopropylamine (2 M isopropylamine hydrochloride, 500 mM EDC-HCl, 500 mM HOBt) was added thereto, and reacted with stirring at 2000 rpm for 1 hour. Through this operation, α2,6-sialic acid and α2,3-sialic acid were converted into isopropylamide and the lactone form, respectively. Subsequently, the resultant was diluted with 120 μL of ACN, which was added to a GL Tip Amide (GL Science Inc.) and passed therethrough by centrifugation at 4000×g to allow the glycan to be adsorbed on a carrier including an amide group for HILIC. Then, 20 to 200 μL of 90% ACN 4% methylamine solution as the amidation reaction solution was passed therethrough for an amidation reaction. Further, 100 μL of 90% ACN 0.1% TFA was passed twice therethrough for washing, and finally 20 μL of H$_2$O was passed twice therethrough for elution of the glycan, and the eluate was subjected to evaporation to dryness by using a SpeedVac. Thereafter, the resultant was further desalted with a Stage Tip Carbon, and subjected to on-target 3AQ, as in the above examination, followed by mass spectrometry.

FIG. 9(a) to (d) each show graphs representing the respective amounts of the amidation reaction solution and production ratios. It was found that aminolysis proceeded in an almost exclusive manner for all of (a) to (d). When the amount of the amidation reaction solution was as small as 20 μL, the time of contact between the carrier and the amidation reaction solution was expected to be several tens of seconds at most, suggesting that the reaction of aminolysis is very quickly occurred.

Examination on Amidation Reaction after Purification with HILIC

By using the operation as in the above examination, a glycan was released from α2,3-SGP, and a lactonization reaction solution containing isopropylamine was added to the glycan for reaction, and ACN was added thereto for dilution, and the glycan was allowed to be adsorbed on an HILIC carrier. Thereafter, 100ᵃ of 90% ACN 0.1% TFA solution was passed twice therethrough for washing, and finally 20ᵃ of $H_2O$ was passed twice therethrough for elution of the glycan. Thereto, 6.7ᵃ of 40% methylamine aqueous solution was added to form an amidation reaction solution containing methylamine with a final concentration of 10%, and the resultant was lightly stirred and then left to stand at room temperature for 2 minutes for an amidation reaction. Thereafter, the solvent was removed by using a SpeedVac, and the resultant was further desalted with a Stage Tip Carbon, and subjected to on-target 3AQ, as in the above examination, followed by mass spectrometry.

Figure 9:
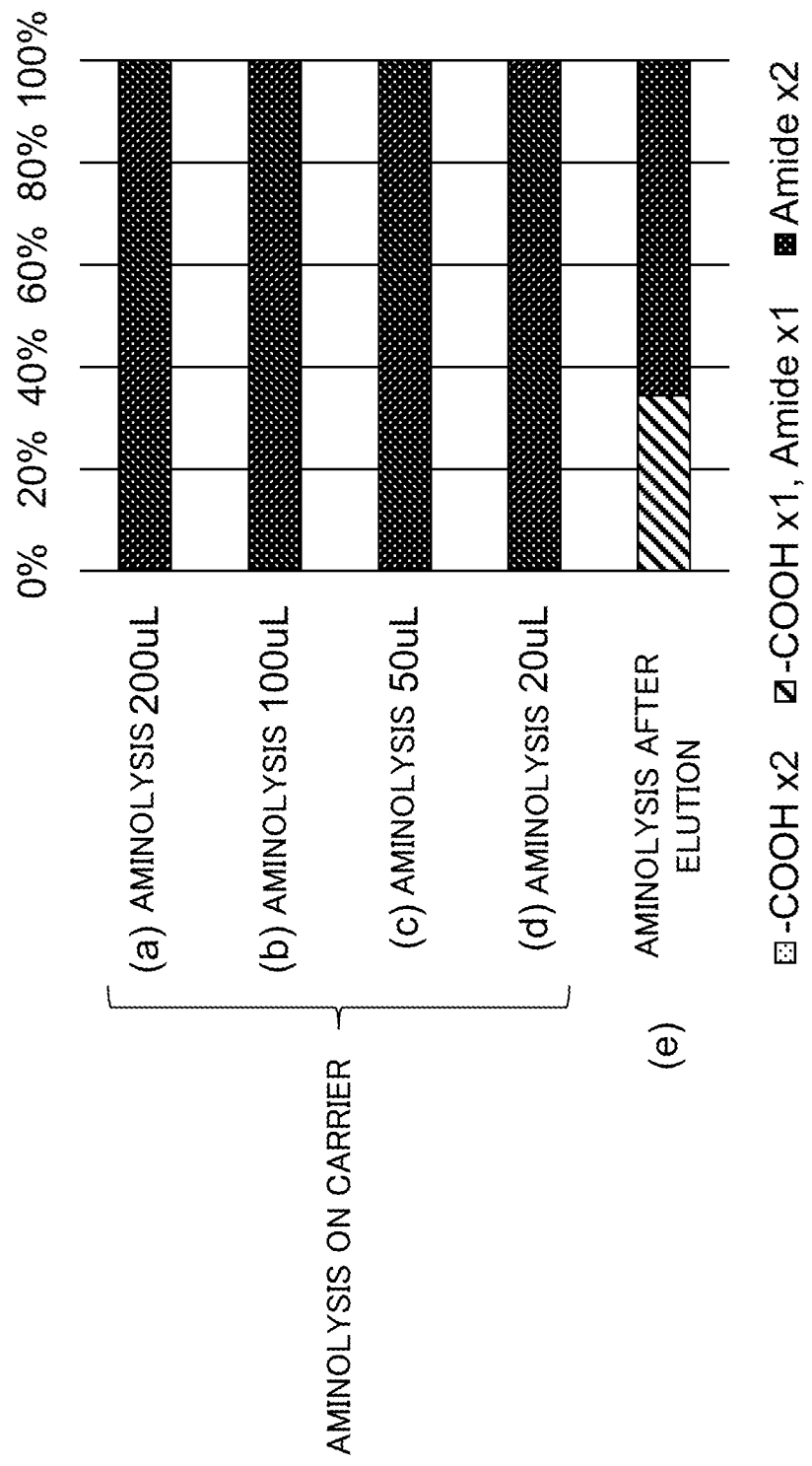
FIG. 9 shows graphs representing respective production ratios of reaction products obtained when a glycan released from α2,3-sialylglycopeptide was subjected to a lactonization reaction and then bonded to an HILIC carrier and the resultant was subjected to an amidation reaction before or after elution.

FIG. 9(e) shows the result. Although the lactones in the sample were generally methylamidated, a product of hydrolysis was also detected. The reason is, in our interpretation, that after the lactonization reaction solution containing isopropylamine was removed by the HILIC carrier, a part of the lactones underwent hydrolysis during the process of washing the carrier. Therefore, although the amidation reaction solution may be added to a sample eluted from an HILIC carrier, it is preferable to add the amidation reaction solution in a state in which a sample is adsorbed on an HILIC carrier, for the purpose of causing aminolysis for substantially all lactones to maximize the reaction efficiency.

The invention claimed is:

1. A method for preparing a sample comprising a glycan, the method comprising:
performing a lactonization reaction in which at least a part of sialic acids included in the glycan is lactonized; and
performing an amidation reaction in which lactones of lactonized sialic acids are amidated by aminolysis based on an interaction between an amino group and a lactone through addition of an amidation reaction solution to the sample, wherein the amidation reaction solution comprises ammonia, an amine, or a salt thereof is reacted with the lactonized sialic acids, wherein the concentration of ammonia, an amine, or a salt thereof in the amidation reaction solution is 0.5 M or more, wherein:
the amine is a primary amine;
pH of the amidation reaction solution is 7.7 or higher; and
in the lactonization reaction, at least one selected from the group consisting of α2,3-sialic acid, α2,8-sialic acid, and α2,9-sialic acid among the sialic acids is lactonized, wherein an operation that reacts the sample with a dehydration condensation agent is not performed after the addition of the amidation reaction solution to the sample, wherein: the amidation reaction solution does not include a dehydration condensation agent that is reacted with the lactones, and wherein only contacting the sample with the amidation reaction solution is performed for the amidation reaction.

2. The method for preparing a sample according to claim 1, the method further comprising removing the lactonization reaction solution from the sample after the lactonization reaction.

3. The method for preparing a sample according to claim 1, wherein: a time during which the sample is in contact with the amidation reaction solution for the amidation reaction is shorter than 30 minutes.

4. The method for preparing a sample according to claim 1, wherein: the amine includes an alkyl group.

5. The method for preparing a sample according to claim 4, wherein: the alkyl group is unbranched.

6. The method for preparing a sample according to claim 1, wherein: the amine includes at least one of an allyl group and a hydroxy group.

7. The method for preparing a sample according to claim 1, wherein: pH of the amidation reaction solution is 8.0 or higher.

8. The method for preparing a sample according to claim 1, wherein: in the lactonization reaction, at least a part of the sialic acids is lactonized through addition of a lactonization reaction solution to the sample, the lactonization reaction solution comprising a dehydration condensation agent that is reacted with the sialic acids included in the glycan.

9. The method for preparing a sample according to claim 8, wherein: the lactonization reaction solution further comprises a nucleophilic agent that is reacted with the sialic acids included in the glycan; the nucleophilic agent differs in mass from the ammonia or the amine used in the amidation reaction; and a part of the sialic acids is lactonized based on the linkage type of the sialic acid through addition of the lactonization reaction solution to the sample, and at least a part of the nucleophilic agent is linked to another part of the sialic acids.

10. The method for preparing a sample according to claim 9, wherein: α2,3-sialic acid is lactonized and α2,6-sialic acid is linked to a part of the nucleophilic agent through addition of the lactonization reaction solution to the sample.

11. The method for preparing a sample according to claim 1, wherein: the sample is contacted with the amidation reaction solution in a state in which the sample is bonded to or adsorbed on a solid phase carrier.

12. The method for preparing a sample according to claim 1, wherein: a solvent of the amidation reaction solution comprises an organic solvent.

13. An analysis method comprising: preparing a sample by using the method for preparing a sample according to claim 1; and analyzing the prepared sample.

14. The analysis method according to claim 13, wherein: the prepared sample is analyzed through at least one of mass spectrometry and chromatography.

15. A method for preparing a sample comprising a glycan, the method comprising:
performing a lactonization reaction in which at least a part of sialic acids included in the glycan is lactonized; and
performing an amidation reaction in which lactones of lactonized sialic acids are amidated through addition of an amidation reaction solution to the sample, wherein the amidation reaction solution comprises ammonia, an amine, or a salt thereof is reacted with the lactonized sialic acids to open lactone rings and amidate lactones of the lactonized sialic acids, and wherein:

the amine is a primary amine;

pH of the amidation reaction solution is 7.7 or higher; and in the lactonization reaction, at least one selected from the group consisting of α2,3-sialic acid, α2,8-sialic acid, and α2,9-sialic acid among the sialic acids is lactonized, wherein the amidation reaction solution does not include a dehydration condensation agent that is reacted with the lactones, and wherein an operation that reacts the sample with a dehydration condensation agent is not performed after the addition of the amidation reaction solution to the sample.

16. The method of claim 15, wherein the lactone rings of the lactonized sialic acids are opened by aminolysis, and do not require hydrolysis.

* * * * *